(12) United States Patent
Cordona et al.

(10) Patent No.: US 7,220,874 B2
(45) Date of Patent: May 22, 2007

(54) ESTERIFICATION OF XANTHOPHYLLS

(75) Inventors: Mario D. T. Cordona, Nuevo Leon (MX); Gustavo Rodriquez, Sinaloa (MX)

(73) Assignee: DSM IP Assets B.V., Geleen (NL)

( * ) Notice: Subject to any disclaimer, the term of this patent is extended or adjusted under 35 U.S.C. 154(b) by 458 days.

(21) Appl. No.: 10/401,102

(22) Filed: Mar. 26, 2003

(65) Prior Publication Data

US 2003/0229239 A1    Dec. 11, 2003

Related U.S. Application Data

(60) Provisional application No. 60/368,190, filed on Mar. 26, 2002.

(51) Int. Cl.
  *C07C 53/00*    (2006.01)
(52) U.S. Cl. .................. 554/229; 554/230; 554/223; 554/224; 560/259
(58) Field of Classification Search ............... 560/259, 560/260; 554/229
  See application file for complete search history.

(56) References Cited

U.S. PATENT DOCUMENTS

| | | | |
|---|---|---|---|
| 4,883,887 A | 11/1989 | Bernhard et al. | |
| 5,523,494 A | 6/1996 | Torres-Cardona et al. | |
| 5,973,211 A | 10/1999 | Rodriguez | |
| 5,998,678 A | 12/1999 | Sanroma Virgili et al. | |
| 2002/0169334 A1* | 11/2002 | Levy et al. | 554/221 |
| 2004/0158097 A1* | 8/2004 | Torres-Cardona et al. | 560/259 |

FOREIGN PATENT DOCUMENTS

| | | |
|---|---|---|
| WO | WO 02/068385 A2 | 9/2002 |
| WO | WO 03/003848 A1 | 1/2003 |

OTHER PUBLICATIONS

Molnar, et al. "Preparation of Partially Acetylated Carotenoids," *Helvetica Chimica Acta*, vol. 85, pp. 2349-2357, 2002.

\* cited by examiner

*Primary Examiner*—Amelia A. Owens
(74) *Attorney, Agent, or Firm*—Nixon & Vanderhye P.C.

(57) ABSTRACT

Lutein and zeaxanthin, the main carotenoids in marigold flowers, and capsanthin and capsorubin, the main carotenoids in red peppers are esterified mainly with C-18 fatty acids. The pigments were re-esterified without isolating them from the natural saponified extract using carboxylic acids in the range of C-1 to C-12 and their corresponding metallic salts in the presence of a catalyzing agent. Both the diester and monoester forms were obtained. It is expected that the pigment esters with a fatty acid of 12 or less carbons will have a better digestibility than the esters of xanthophylls in their natural state and better stability than the hydrolyzed xanthophylls. This will result in a better pigmentation capacity of the carotenoids for poultry or aquaculture.

29 Claims, No Drawings

ESTERIFICATION OF XANTHOPHYLLS

RELATED APPLICATIONS

This application claims priority to U.S. provisional application No. 60/368,190, filed Mar. 26, 2002, which is incorporated herein by reference in its entirety.

BACKGROUND OF THE INVENTION

1. Field of the Invention

The present invention relates to chemical methods to esterify xanthophylls obtained from diverse sources including marigold flowers and red peppers.

2. Description of the Related Art

During several decades xanthophylls have been subjected to constant research due to their use both in human and animal consumption. In the poultry business the color of the egg yolk as well as that of the broilers skin is an important factor related to quality and consumer preference. It is because of this that there is a constant effort to provide poultry formulations including better pigmenting agents where their physical and chemical characteristics allow a better absorption thus rendering optimal pigmentation at lower costs.

Xanthopylls in marigolds are esterified mainly with palmitic, stearic and myristic acids and others of less importance (Alam et al. (1968) Lipids 3(2): 183–184). Egg laying hens make better use of lutein esters than the crystalline form of free lutein (Philip et al. (1976) J. Food Sci. 41:23–25) indicating that it could be due to a better solubility of the esters in lipids. Similar results were reported in the absorption of capsanthin from red peppers (Hamilton et al. (1990), Poult. Sci 69: 462–470). It was found that free lutein was better absorbed by broilers than the esters (Fletcher et al. (1986) Poult. Sci. 65: 1708–1714). Tyczkowski and Hamilton (1986) demonstrated that lutein is found free in the blood serum of broilers and that it is deposited in the skin as an ester after enzymatic transformation. Differences were observed between the polar interactions derived from the esterified and free forms of zeaxanthin and some of their rheological consequences (Zsako, et al. (1987) Rev. Roum. Chim. 32: 739–748). As the carbon chain that forms the fatty acid of the carotenoid ester is shorter, there is less steric hindrance and greater polarity. Regarding the relative polarity of several carotenoids, the allylic hydroxy is up to 50% more polar than the acetyl group thus conferring zeaxanthin a higher polarity than lutein and also lutein being more polar than the acetylated derivatives of zeaxanthin or lutein (Krinsky (1963) An. Biochem. 6: 293–302). The digestibility of the fatty acids in broilers as well as layers is inversely related to the length of the carbon chain (Yoshida, et al. (1970) Agr. Biol. Chem. 34(11): 1668–1675). Those with better bioavailability have between 5 to 12 carbons and those with lower bioavailability have less than 5 carbons (except acetic acid) or more than 12 carbons. A similar relation applies for the esters indicating that methyl, ethyl, propyl, butyl, amyl and hexyl derivatives of the fatty acids mentioned above are better absorbed by both broilers and layers. The studies by Tyczkowski and Hamilton indicate that the length of the carbon chain, and the saturation and concentration of the lipids included in the poultry diets notably influence the lutein absorption. A better uptake is observed when the fatty acids are of short chain and/or unsaturated.

The above is explained based on the micellar theory of digestion and the polarity of the oxycarotenoids. In broilers it has been demonstrated that lutein, zeaxanthin and other carotenoids are better absorbed in their free form than as natural esters like palmitate, stearate, myristate, etc, having a definite effect in skin pigmentation. In broilers, lutein from marigolds is hydrolyzed before absorption in the intestine and transported in this form to different tissues, but before deposition in the skin the pigment is re-esterified (Martin-Garmendia et al. (1981) Comp. Biochem. Physiol. $70^a$: 619–621). It is important to mention that the esterified xanthophylls have a better stability against several adverse physical and chemical factors than their equivalent hydrolyzed forms. Breivik, et al. (WO 03/003848A1) describe the use of a diester of astaxanthin prepared with an omega-3 fatty acid and/or a short chain carboxylic acid for enhancing the growth of farmed fish.

Traditionally esterification of marigold carotenoids is carried out for analytical purposes by making acetylated derivatives or partially acetylated derivatives by reacting the carotenoid with acetic anhydride in the presence of pyridine (Eugster (1995) Carotenoids: Vol. 1A, G. Britton, ed. page 74, Birkhauser; Molnar (2002) Helv. Chim. Acta 85:2349).

Bernhard, et al. (U.S. Pat. No. 4,883,887) developed several intermediates for the synthesis of the same carotenoids among which are mentioned their mono and diacetylated derivatives using for this process acetic anhydride at a very low temperature.

Torres Cardona et al. (U.S. Pat. No. 5,523,494), describe a process for esterification of marigold xanthophylls using acetic or propionic anhydride obtaining the corresponding acetate or propionate of the carotenoid. The presence of water in the reaction medium makes handling of the reaction difficult due to the violent reaction of the anhydride. This situation favors intensive degradation of the pigments and the accumulation of acetic or propionic acid as well as their respective salts.

Others have reported processes for esterification of carotenoids using chlorides of fatty acids which are needed to bind to the chain. No process has been reported for commercial purposes in which acetic anhydride or acid chlorides have not been used in some way or another for the esterification of marigold xanthophylls.

SUMMARY OF THE INVENTION

In one embodiment, a process for the esterification of the xanthophylls is disclosed which includes the steps of:
  reacting an extract containing xanthophylls with a carboxylic acid having a carbon chain length between 1 to 12 in the presence of a catalyst; and
  continuously removing the water generated from the reaction to facilitate the transformation to xanthophyll esters; and
  collecting the xanthophyll ester product.

In a preferred embodiment, the xanthophylls in the extract have been either saponified or isomerized before esterification. In some embodiments, the xanthophylls in the extract have been saponified and isomerized in a previous step. In a preferred embodiment, the extract is prepared from a substrate selected from the group consisting of marigold flowers, red peppers, alfalfa, yellow corn, corn gluten, algae, and purified pigments thereof. In one embodiment, the xanthophylls include hydroxycarotenoids.

In one preferred embodiment of the invention, the substrate is marigold flowers and the carotenoids include lutein, zeaxanthin and beta-cryptoxanthin. In another preferred embodiment of the invention, the substrate is red peppers and the carotenoids include capsanthin, capsorubin, zeaxanthin and lutein.

The carbon chains of 1 to 12 are either saturated or unsaturated. The carboxylic acids are of either synthetic or natural origin. "Synthetic origin" means made from an artificial source such as a chemical synthesis. "Natural origin" means having a natural source such as a plant or animal source. Carboxylic acids of natural origin include but are not limited to those found in vegetable fats and oils. In a more preferred embodiment, the carbon chain length is between 5 and 12.

In one embodiment, the catalyst is a mineral acid such as sulfuric acid, phosphoric acid, hydrochloric acid, hydrobromic acid, nitric acid, similar acids and mixtures thereof. In an alternate embodiment, the catalyst is an organic acid such as p-toluenesulfonic acid, ethylsulfuric acid, ethanedisulfuric acid, benzenesulfuric acid, dodecanesulfonic acid, chloroacetic acid, dichloroacetic acid, trichloroacetic acid, boron trifluoride, and pyridine salts. In another embodiment, the catalyst is a metallic chloride including but not limited to zinc chloride, stannous chloride, aluminum chloride, similar metal salts, and mixtures thereof. In a preferred embodiment, the catalyst is used in quantities from 0.001 to 0.1 parts by weight in relation the total reaction mixture.

In one embodiment of the invention, small amounts of a polar solvent in the range of 0.001 to 0.1 parts by weight in relation to the substrate are used. In a preferred embodiment, the polar solvent is selected from the group including a ketone, a chlorinated hydrocarbon, an amine, dimethyl sulfoxide, dioxane, and tetrahydrofuran. However, any solvent that may improve mass transference during esterification, thus speeding up the reaction, may be used.

In one embodiment of the invention, the carboxylic acid is used in a proportion of 0.1 to 5 parts by weight for each part of carotenoid. In a more preferred embodiment of the invention, the carboxylic acid is used in a proportion of 0.3 to 2 parts by weight for each part of carotenoid: In a preferred embodiment, the reaction takes place at a temperature between about 25° C. and 140° C. In a more preferred embodiment, the reaction takes place at a temperature between about 50° C. and 110° C. In one embodiment of the invention, the reaction takes place at atmospheric pressure. In an alternate embodiment, the reaction takes place with a vacuum of 1 to 25 inches Hg. In one embodiment, the reaction can be carried out under a stream of an inert gas. In a preferred embodiment, the inert gas is selected from the group including nitrogen, carbon dioxide or mixtures thereof. In a preferred embodiment, the reaction time is between about 30 min to 18 hr. In a more preferred embodiment, the reaction time is between about 2 to 12 hrs.

In one embodiment of the invention, the esterified xanthophylls include monoesterified derivatives, diesterified derivatives and mixtures thereof. These derivatives may be obtained in any proportion by reaction with carboxylic acids which may be saturated or unsaturated and which have a carbon chain of 1 to 12 carbons. In a preferred embodiment, the esterification is selectively related to the carboxylic acid used and controlled by the processing conditions. In other words, the bioavailability of the xanthophyll ester product is selectively related to the carboxylic acid used. In a preferred embodiment, the water generated by the reaction is eliminated continuously and selectively from the process. In one preferred embodiment, a conversion of more than 90% monoesterified xanthophylls is achieved. In an alternate preferred embodiment, a conversion of more than 90% diesterified xanthophylls is achieved.

Further aspects, features and advantages of this invention will become apparent from the detailed description of the preferred embodiments which follow.

DETAILED DESCRIPTION OF THE PREFERRED EMBODIMENT

A process useful for the esterification of xanthophylls found in the saponified and/or isomerized extracts of marigold flowers (*Tagetes erecta* L) and red peppers (*Capsicum annum* L) is described. The term "xanthophylls" includes any of several yellow accessory pigments which are found in plant leaves, egg yolks, and human blood plasma. These pigments are oxygen derivatives of carotenoids. The more general term "carotenoids" refers to a group of red, orange, purple or yellow pigments typically found as accessory pigments in plants and some fungi. In the present application, the terms "xanthophylls" and "carotenoids" are used somewhat interchangeably. The disclosed process uses carboxylic acids of the series C-1 to C-12 and their respective metallic salts in presence of an excess of the same acid that works also as a solvent. A catalyst is included which can be a mineral acid like sulfuric acid, hydrochloric acid or an organic acid like p-toluenesulfonic acid, boron trifluoride and pyridine salt or any metallic chloride like zinc chloride, tin chloride, aluminum chloride or others and also mixtures of the catalysts mentioned above.

The carotenoids esterified in this manner are useful for pigmentation of broilers skins and egg yolks and may also be used in other animal feeds or for human consumption. They may also serve as immunostimulants and pigmenting agents in aquaculture mainly with some crustaceans and salmonids. They can also have nutraceutical applications in humans acting as antioxidants and in the prevention and treatment of age related macular degeneration, some cancers and vascular and cardiac problems. These carotenoids can also be intermediary compounds for chemical synthesis of other carotenoids.

Any xanthophyll-containing material may be used in the disclosed process. However, in a preferred embodiment, the substrates to carry out this process are saponified marigold and red pepper extracts, free lutein or zeaxanthin from the same source, and saponified and isomerized extracts with moderate or high levels of zeaxanthin prepared by the procedures described by Rodriguez (U.S. Pat. No. 5,973,211), Torres-Cardona et al. (U.S. Pat. No. 5,523,494), Sanroma et al. (U.S. Pat. No. 5,998,678), Bernhard et al. (U.S. Pat. No. 4,883,887), or mixtures of the above.

The saponified extracts of marigold and red pepper normally are in a highly alkaline state with excess of sodium or potassium hydroxide. With these materials, aqueous mixtures containing from 5 to 20 grams per kilogram of xanthophylls were prepared. The mixture was then neutralized to a pH between 2 and 5 at a temperature between 25 to 90° C. with a 5 to 25% solution of acetic acid or a diluted solution of the acid to be used in the esterification reaction. The oily residue was separated from the aqueous phase and this acid containing water may be recycled in further reactions. The remaining oily residue contains mainly the natural fatty acids from the extracts and the xanthophylls of interest. This fraction was then put to an evaporation step using vacuum so as to eliminate the water. The residue remains impregnated with the carboxylic acid and its sodium or potassium salt. Then, between 0.1 to 5 parts of the carboxylic acid per part of extract were added and also between 0.001 to 0.1 parts of catalyst in relation to the total mixture. Optionally a polar or slightly polar solvent like some ketones, amines, halogenated hydrocarbons, dimethyl sulfoxide, dioxane, or other in which the reactants may be soluble but non-reactive may be used adding between 0.001 and 0.1 parts per total volume. These solvents have the purpose of creating a minimal interface in which the mass transfers are more efficient and reaction times are reduced.

The reaction takes place between 25 and 150° C. and preferably between 50 and 100° C. with moderate agitation and continuous distillation of water which is being generated as the reaction advances. The reaction can take place at atmospheric pressure but it is preferred to work at slightly reduced pressure using a vacuum between 1 to 25 inches of Hg. Depending on the selected operating conditions the reaction time may fluctuate between 30 min to 18 hours but preferably between 2 to 12 hours.

The esterification process described is possible only when the reaction equilibrium is displaced towards the right. This is facilitated where one of the reaction products is continuously removed and these are either the esters or water or by keeping an excess of one of the reactants which are the carotenoids or the carboxylic acid. The shorter the chain in the carboxylic acid the less steric hindrance which in turn increases the speed of reaction with the alcohol (Groggins (1958) Unit Processes in Organic Synthesis, p. 698, McGraw-Hill Publishers). In this way the C-18 fatty acids from the pigment which remain in the extract stay in their free form since their reactivity under the process conditions described is very low. The following is the reaction sequence:

ESTERIFICATION OF CAROTENOLS

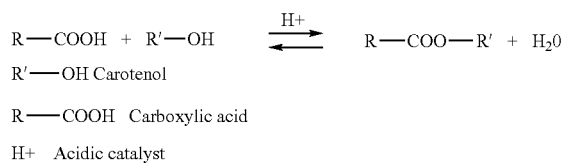

R'—OH Carotenol

R—COOH Carboxylic acid

H+ Acidic catalyst

During the reaction, conditions are maintained to continuously remove water by distillation that is being formed as a product of the esterification. This operation allows the conversion of the oxycarotenoid to an ester. What we have is a typical esterification reaction that has been selectively adapted to esterify xanthophylls, using an interface that makes a notable improvement in mass transference and consequently provides an acceptable speed of reaction to conserve the integrity of the carotenoids.

The progress of the reaction was monitored using the official method for analysis of xanthophylls of the Association of Official Analytical Chemists and testing by HPLC and IR Spectroscopy. When the esterification was completed the excess acid was removed from the reaction mixture and the resultant oil may be formulated according to the applications it will have such as aquaculture, poultry use or human consumption.

It will be understood by those of skill in the art that numerous and various modifications can be made without departing from the spirit of the present invention. Therefore, it should be clearly understood that the forms of the present invention are illustrative only and are not intended to limit the scope of the present invention.

EXAMPLES

Example 1

100 gm of saponified marigold extract that contained 55 grams of xanthophylls for each kg of extract and in which 85% of the pigments was lutein and 6% zeaxanthin were heated to 90° C. with moderate agitation. Then a 12% aqueous solution of acetic acid was added so as to have a final pH of the mixture between 3 and 4. After 15 minutes more of mixing, the agitator was stopped and a two phase separation was obtained. The aqueous phase was decanted. The remaining oil phase was kept at 90° C. with a vacuum of 9 in. Hg to eliminate water excess until less than 3% moisture was obtained. During this dehydration step, 0.1% of ethoxyquin was added as antioxidant. After drying, 50 gm of acetic acid and 4 gm of p-toluenesulfonic acid were added and the reaction was continued for 8 hours with continuous water distillation. At the end of the reaction 93% diacetates, 4% monoacetates and 2% dihydroxypigments were obtained using the AOAC methodology for testing.

Example 2

150 gm of a saponified red pepper oleoresin containing 37.6 gm/Kg of total carotenoids of which 37% was capsanthin, 1% capsorubin and 12% other red pigments with approximately 50% yellow pigments of which 6% was zeaxanthin and 20% unsaponifiable carotenes was mixed with 226 gm of water until evenly dispersed, keeping the temperature between 70 to 75° C. Then 50 gm of acetic acid were added. A pH of 4.5 was obtained and a two phase system was formed. The bottom aqueous layer was decanted and another 75 gm of acetic acid was added. Remaining water was removed by vacuum distillation (20 in Hg) at a temperature between 70 to 75° C. until less than 4% moisture was obtained. Then 10 gm of p-toluenesulfonic acid in 7 gm of acetic acid were added for reaction at 100° C.

The water produced by the reaction was distilled using a slight vacuum (0 to 2 in. Hg). After 10 hours at these conditions the reaction was cooled to 45° C. and washed twice with 150 ml of water to remove the excess acid and catalyst. The pigments in the end product contained 70% diacetates and 10% monoacetates.

Example 3

300 gm of marigold extract which was saponified and isomerized by the method reported by Rodriquez (U.S. Pat. No. 5,973,211, which is incorporated herein by reference) and which had 45 grams of the total xanthophylls per kilogram of extract. This was used as starting material. Of the xanthophylls content, 65% was zeaxanthin and 25% lutein. The extract was dispersed with moderate agitation in 300 gm of 25% acetic acid solution and the temperature was adjusted to 80° C. Afterwards another 300 gm of the 25% acetic acid solution was added and a pH of approximately 4 was obtained. The mixture was allowed to rest for 5 minutes which was enough time to separate the aqueous phase. Then 0.1% of ethoxyquin was added to the remaining oil and dried at 80° C. with a vacuum of 25 in. Hg until 97% solids was reached. After this, 100 gm of acetic acid and 10 gm of zinc chloride were added and the reaction was continued for 12 hours, distilling the water produced at atmospheric pressure. The product obtained contained 91% diacetates, 6% monoacetates and 3% dihydroxycarotenoids.

Example 4

A marigold extract weighing 300 gm and containing 47 gm of total xanthophylls per kilogram was saponified and isomerized by the method described by Rodriguez (U.S. Pat. No. 5,973,211). 45% of the pigments were zeaxanthin, 40% lutein and 10% beta-cryptoxanthin. This was mixed using moderate agitation with 200 gm of water and the temperature adjusted to 80° C. Then the pH of the mixture was taken between 3 to 4 with a 20% aqueous solution of formic acid. An aqueous phase appeared which was separated by decantation. The resultant oil contained the pigment of interest as well as residual formic acid and moisture. The oil was subjected to a drying process under vacuum until 96% total solids was achieved. Atmospheric conditions were then established and 80 gm of formic acid were added to proceed with the reaction at 90° C. During the 6 hours duration of the reaction, another 50 gm of formic acid was added and the water generated was distilled azeotropically with formic acid. The acid was recuperated by azeotropic distillation for reutilization. At the end of processing, the residual acid was removed completely by washing with water. The product formulated contained a pigment profile of 85% diformates, 11% monoformates and 4% dihydroxy-carotenoids.

Example 5

50 gm of a saponified marigold extract containing high levels of chlorophyll derivatives and 60 gm of total xanthophylls per kilogram of which 86% were lutein and 6% zeaxanthin were dispersed in 50 gm of water and the temperature was taken to 75° C. The pH of the mixture was then adjusted to 4 using a 25% aqueous solution of propionic acid. The mass was allowed to rest until a two phase separation occurred from which the aqueous phase was decanted. Then 0.15% of ethoxyquin was added to the oily extract and dried at 90° C. with a vacuum of 25 in. Hg until more than 95% solids were obtained. 50 gm of propionic acid and 5 gm of sulfonic acid were added. The reaction was carried out with the temperature set at 90° C. and the pressure controlled so as to distill the water produced by the process. During the 8 hours of reaction time another 50 gm of propionic acid were added. At the end of the reaction, the excess acid was washed off with a total of 150 gm of water and the propionic acid was recuperated by azeotropic distillation for further use. The product obtained consisted of 92% dipropionates, 4% monopropionates and 4% dihydroxypigments.

Example 6

300 gm of marigold extract, saponified and isomerized by the method described by Rodriguez (U.S. Pat. No. 5,973,211) was mixed using moderate agitation with 300 gm of water while the temperature was taken to 80° C. The extract had 45 gm of total xanthophylls per kilogram of which 92% was zeaxanthin and 5% beta-cryptoxanthin. The pH was then adjusted between 3 and 4 using a 10% aqueous solution of butyric acid. After stopping agitation the mixture was allowed to separate into two phases and the aqueous phase was decanted. The oil phase was dried to more than 95% solids using vacuum for the distillation. Then 150 gm of butyric acid, 10 gm of p-toluenesulfonic acid and 10 gm of stannous chloride were added and the temperature taken to 90° C. while applying vacuum sufficient enough to continuously remove water generated by the reaction. The reaction time at these conditions was 8 hours and the end product presented 91% dibutyrates, 6% monobutyrates and 3% dihydroxycarotenoids.

Example 7

100 gm of a saponified marigold extract containing 60 gm of total xanthophylls where 86% was lutein and 6% zeax-anthin were dispersed in 100 gm of water with gentle mixing. The temperature was raised to 80° C. The pH was then taken between 4 and 5 using a 20% aqueous solution of acetic acid. A two layer system was formed from where the lower aqueous phase was separated and eliminated. The remaining oil was vacuum dried until more than 96% total solids was obtained. Then 75 gm of acetic acid, 7 gm of p-toluensulfonic acid and 3 gm of dimethyl sulfoxide were added. The temperature was fixed at 100° C. and the water generated by the reaction was allowed to distill freely. After 6 hours, the reaction mixture was cooled to 45° C. and the residual acid, catalyst and solvent were washed with water. The product obtained had 92% diacetates, 4% monoacetates and 4% dihydroxycarotenoids.

Example 8

The product obtained in Example 3 was integrated in a premix which contained silica and wheat bran as main carriers and ethoxyquin and butylated hydroxyanisole as antioxidants to make a powder with 10 gm of total xanthophylls per kilogram.

In an experimental farm 100 egg-laying hens of the Dekalb breed were selected and identified as "Experimental Group". Another group of 100 hens was identified as "Control Group". All hens were 50 weeks of age and treated equally, including the same formulation, the pigment source being the only difference. For the "Experimental Group" 12 ppm of pigment prepared as described in Example 3 were included in the diet. For the "Control Group" a typical pigmenting formulation was used and consisted of 8.4 ppm of saponified marigold xanthophylls plus 4.2 ppm of saponified red pepper xanthophylls. The yolk pigmentation was measured in both groups each week during six consecutive weeks using a Minolta CR-300 reflectance calorimeter. The Lab scale of the colorimeter was used for the measurements. Quantification of surface color was determined by the CIELAB method (K. McLaren in Developments in Food Colours-1, John Walford, ed. Applied Science Publishers LTD, London). The L* values were up to 10% higher in the "Control Group". The values of b* were about 10% higher in the "Experimental Group" compared to the control and as expected the a* values also turned out 3 to 4 times higher in the "Experimental Group". Measuring total xanthophylls by extraction of the egg yolk and spectrophotometric determination, 15 to 20 ppm were detected in the "Control Group" compared to 40 to 50 ppm in the "Experimental Group".

Example 9

The field test described in Example 7 was repeated using the product obtained in Example 6. The total xanthophylls determination showed similar results for pigment deposition in the egg yolk for both the "Control Group" and the "Experimental Group". Nevertheless the L* and b* values were about 10% higher in the "Experimental Group" and the a* values were detected at one to two times higher. The results of Examples 8 and 9 indicate that the esterified xanthophylls of the present invention are better digested and absorbed compared to a typical pigmenting composition containing saponified xanthophylls.

What is claimed is:

1. A process for the esterification of xanthophylls, wherein the xanthophylls consist essentially of lutein and zeaxanthin, comprising:

reacting an extract which is prepared from a substrate selected from the group consisting of marigold flowers, red peppers, alfalfa, yellow corn, corn gluten, algae, and purified pigments thereof and which contains xanthophylls with a carboxylic acid having a carbon chain length between 1 to 12 in the presence of a catalyst;

continuously removing the water generated from the reaction to facilitate the transformation to xanthophylls esters; and collecting the xanthophylls ester product.

2. The process of claim 1, wherein the xanthophylls are reacted with a carboxylic acid having a carbon chain length between 5 and 12.

3. The process of claim 1, wherein at least one of said carbon chain of 1 to 12 is saturated.

4. The process of claim 1, wherein at least one of said carbon chain of 1 to 12 is unsaturated.

5. The process of claim 1, wherein the carboxylic acids are of synthetic origin.

6. The process of claim 1, wherein the carboxylic acids are of natural origin.

7. The process of claim 1, wherein the catalyst is a mineral acid selected from the group consisting of sulfuric acid, phosphoric acid, hydrochloric acid, hydrobromic acid, nitric acid, and mixtures thereof.

8. The process of claim 1, wherein the catalyst is an organic acid selected from the group consisting of p-toluenesulfonic acid, ethylsulfuric acid, ethanedisulfuric acid, benzenesulfuric acid, dodecanesulfonic acid, chloroacetic acid, dichloroacetic acid, trichloroacetic acid, boron trifluoride, and pyridine salts.

9. The process of claim 1, wherein the catalyst is a metallic chloride selected from the group consisting of zinc chloride, stannous chloride, aluminum chloride and mixtures thereof.

10. The process of claim 1, wherein the catalyst is used in quantities from 0.001 to 0.1 parts by weight in relation the total reaction mixture.

11. The process of claim 1, in which small amounts of a polar solvent in the range of 0.001 to 0.1 parts by weight in relation to the substrate are used.

12. The process of claim 11, wherein the polar solvent is selected from the group consisting of a ketone, a chlorinated hydrocarbon, an amine, dimethyl sulfoxide, dioxane, and tetrahydrofuran.

13. The process of claim 1, wherein the carboxylic acid is used in a proportion of 0.1 to 5 parts by weight for each part of carotenoid.

14. The process of claim 13, wherein the carboxylic acid is used in a proportion of 0.3 to 2 parts by weight for each part of carotenoid.

15. The process of claim 1, wherein the reaction takes place at a temperature between about 25° C. and 140° C.

16. The process of claim 15, wherein the reaction takes place at a temperature between about 50° C. and 110° C.

17. The process of claim 1, wherein the reaction takes place at atmospheric pressure.

18. The process of claim 1, wherein the reaction takes place with a vacuum of 1 to 25 inches Hg.

19. The process of claim 1, wherein the reaction can be carried out under a stream of an inert gas selected from the group consisting of nitrogen, carbon dioxide or mixtures thereof.

20. The process of claim 1, wherein the xanthophylls ester product comprises monoesterified xanthophylls, diesterified xanthophylls, and mixtures thereof.

21. The process of claim 1, wherein the reaction time is between about 30 mm to 18 hr.

22. The process of claim 21, wherein the reaction time is between about 2 to 12 hrs.

23. The process of claim 1, wherein the water generated by the reaction is eliminated continuously and selectively from the process.

24. The process of claim 1, wherein a bioavailability of the xanthophyll ester product is selectively related to the carboxylic acid used.

25. The process of claim 1, wherein more than 90% of said xanthophylls esters are monoesterified xanthophylls.

26. The process of claim 1, wherein more than 90% of said xanthophylls esters are diesterified xanthophylls.

27. The process of claim 1, wherein the xanthophylls in the extract were isomerized and/or saponified in a previous step.

28. A process for the esterification of xanthophylls, wherein the xanthophylls consist essentially of lutein, zeaxanthin and beta-cryptoxanthin, comprising:

reacting an extract from marigold flowers with a carboxylic acid having a carbon chain length between 1 to 12 in the presence of a catalyst;

continuously removing the water generated from the reaction to facilitate the transformation to xanthophylls esters; and collecting the xanthophylls ester product.

29. A process for the esterification of xanthophylls, wherein the xanthophylls consist essentially of lutein, zeaxanthin, capsanthin and capsorubin, comprising:

reacting an extract from red peppers with a carboxylic acid having a carbon chain length between 1 to 12 in the presence of a catalyst;

continuously removing the water generated from the reaction to facilitate the transformation to xanthophylls esters; and collecting the xanthophylls ester product.

* * * * *